United States Patent [19]

Forgar et al.

[11] Patent Number: 4,838,868
[45] Date of Patent: Jun. 13, 1989

[54] TAPE FOR SECURING A HYPODERMIC NEEDLE

[75] Inventors: Monica Forgar; Kerstin Björnson-Ljungblom, both of Gothenborg, Sweden

[73] Assignee: Molnlycke AB, Gothenborg, Sweden

[21] Appl. No.: 61,632

[22] Filed: May 14, 1987

[30] Foreign Application Priority Data

May 23, 1986 [SE] Sweden ............................. 8602360

[51] Int. Cl.⁴ .............................................. A61M 5/32
[52] U.S. Cl. ..................................... 604/180; 128/877
[58] Field of Search ................ 604/180, 174; 128/D6, 128/D26, 133, 126

[56] References Cited

U.S. PATENT DOCUMENTS

| | | | |
|---|---|---|---|
| 3,138,158 | 6/1964 | Gordon et al. ..................... | 128/D26 |
| 3,422,817 | 1/1969 | Mishkin et al. ..................... | 128/133 |
| 3,430,300 | 3/1969 | Doan ................................ | 128/D26 |
| 3,826,254 | 7/1974 | Mellor .............................. | 128/133 |
| 3,834,380 | 9/1974 | Boyd ................................ | 128/133 |
| 3,885,560 | 5/1975 | Baldwin ............................ | 128/D26 |
| 3,918,446 | 11/1975 | Buttaravoli ........................ | 128/133 |
| 3,973,565 | 8/1976 | Steer ................................ | 604/180 |
| 4,122,857 | 10/1978 | Haerr ................................ | 128/133 |
| 4,142,527 | 3/1979 | Garcia .............................. | 128/D26 |
| 4,165,748 | 8/1979 | Johnson ............................ | 128/133 |
| 4,275,721 | 6/1981 | Olson ............................... | 604/180 |
| 4,324,237 | 4/1982 | Buttaravoli . | |
| 4,490,141 | 12/1984 | Lacko et al. ...................... | 604/180 |
| 4,531,942 | 7/1985 | Turner .............................. | 604/180 |
| 4,633,863 | 1/1987 | Filips et al. ....................... | 128/133 |
| 4,737,143 | 3/1988 | Russell ............................. | 128/D26 |

FOREIGN PATENT DOCUMENTS

| | | | |
|---|---|---|---|
| 998901 | 10/1976 | Canada ............................. | 604/180 |
| 0120570 | 10/1984 | European Pat. Off. . | |
| 0414994 | 9/1980 | Sweden . | |
| 1425338 | 2/1976 | United Kingdom ............... | 604/180 |

Primary Examiner—John D. Yasko
Attorney, Agent, or Firm—Young & Thompson

[57] ABSTRACT

The present invention relates to a tape serving the purpose of securing hypodermic needles. The tape includes a carrier layer known per se and attachable over a hypodermic needle fixed in position. The carrier layer is partly cut in its one direction and has on its side intended to face the hypodermic needle and the patient's body an adhesive coating for fastening it to the patient's skin. This adhesive coating, which is covered with release foil portions, extends across the whole attachment area of the carrier layer, one release foil portion simultaneously extending over the non-slit section of that layer, and either one of two additional release foil portions extending over its own respective section of the carrier layer cut or separated by the slit.

2 Claims, 1 Drawing Sheet

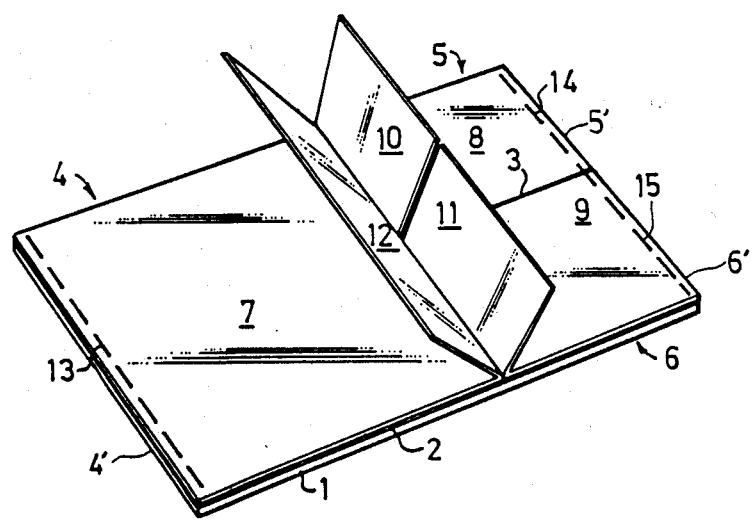

TAPE FOR SECURING A HYPODERMIC NEEDLE

In order to provide optimal freedom from bacterial contamination in the area around the puncture site of a hypodermic needle, the needle must be capable of resting steadily on the body portion of a patient while being firmly held in place, which is particularly important in cases where the needle has to remain in its applied position for prolonged periods of time. Since hypodermic needles are commonly attached or secured with the aid of numerous pieces of adhesive tape or strips, the requirement expressed above has not yet been fully satisfied. When attaching a plurality of adhesive tape strips around the puncture site of a hypodermic needle, the nursing personnel can hardly avoid repeated contact with the area which should be protected from contamination. Because of the large number of tape strips used, the quality of needle securement will further depend on the individual performing the application. Poorly affixed hypodermic needles may give rise both to infections and to painful dislodging of the needle caused by the movements of the patient.

The actual problem of securing hypodermic needles or catheters upon application has however been dealt with per se in prior art teachings. As an example, there has been suggested an intravenous catheter dressing provided with a fixed gauze pad and a backing layer securable over the catheter applied to the patient's skin, said backing layer being cut by a slit in its one direction while having on its side facing the cathether and the patient's skin a coating of adhesive agent. This adhesive surface is in turn coated or covered with two release film portions provided with free pull tabs located in close proximity to one another, one of said release film portions covering the non-slit section of the backing layer and the overlying fixed dressing, and the other film portion covering the slit section of the backing layer. The combination of a partly slit backing layer attachable to the skin of a patient and a fixed dressing has in fact lead to a number of advantages in relation to the method of securing hypodermic needles mentioned in the introduction and carried out with the use of a plurality of tape strips, possibly in combination with a loose gauze pad. Unfortunately however, also this prior art intravenous catheter dressing has failed to provide a fully satisfactory solution to the serious problem of contamination.

Therefore, the present invention has for its object the provision of a novel tape for the purpose of securing hypodermic needles while minimizing the cumbersome contamination problem, providing in addition an improved and better-defined needle securement than has been possible with previously available methods and means.

For the sake of achieving this object, there is provided according to the present invention a tape intended for the securement of hypodermic needles, said tape incorporating a carrier layer which is known per se by the teaching of the aforementioned intravenous catheter dressing and which is attachable over a hypodermic needle fixed in position while being securable to the patient's skin, said carrier layer being partly cut in its one-direction by a slit while having on its side facing the needle and the patient's skin an adhesive coating covered with release foil portions provided with free gripping flaps or pull tabs located in close proximity to one another. According to the invention, the adhesive coating extends all over the carrier layer, whereas one release foil portion extends across the non-slit section of said carrier layer and either one of two further release foil portions extends over its respective section of the layer cut by the slit.

By utilizing a carrier layer designed and equipped as set forth above, there is obtained a tape having a largest possible attachment surface, the novel release foil arrangement reducing to a minimum the risk of the tape loosing its sterility upon application to the body of a patient, producing at the same time a most easily applicable tape which can be affixed without the puncture site of the applied hypodermic needle having to be touched by the nursing staff members.

In order to improve to a still higher degree the hygienic conditions during application of the tape while simultaneously simplifying this process, which is a vital factor particularly when dealing with tapes having very thin carrier layers, the release foil portions according to a particularly suitable embodiment of the invention are more firmly secured to the free ends of the non-slit section of the carrier layer and to the sections of this layer separated by the slit than to the remainder of the carrier layer, for example by means of a perforation, an embossment or the like arrangement.

On their side treated with release agent, the free gripping flaps of the release foil portions may suitably have an embossed surface thereby making them more easily graspable.

The invention will be described in more detail below with the aid of an exemplary embodiment and with reference view of a preferred embodiment of a tape made in accordance with the invention and in its wrapped state when viewed obliquely towards the side intended to face the skin of a patient.

As indicated in the drawing, the inventive tape for securing a hypodermic needle incorporates a carrier layer 1 which can be placed over a hypodermic needle, a catheter or any other similar medical item now shown here and which can be affixed to the skin of a patient, said carrier layer for this purpose being provided with an adhesive coating 2 sticking to the hypodermic needle as well as to the skin of the patient.

The carrier layer 1 may consist of a fibrous material such as fiber fabric, preferably of the spun-lace type with fibers of polyester for example, said fibrous material being pervious both to water and to air. The adhesive coating 2 may, for example, consist of a layer of an acrylate binder, which would render the carrier layer 1 at least essentially water-tight while simultaneously preserving its breathability.

Alternatively, however, an essentially water-tight but air-permeable plastic film consisting of thermoplastic polyurethane for example, could be used for the carrier layer 1, whereas an acrylate binder could be utilized for producing also the adhesive coating 2.

For facilitating securement of the hypodermic needle applied, the carrier layer 1 having its attachment side covered with the adhesive coating 2 is partially cut in its one direction by a slit 3, forming in this manner a non-slit section 4 and two flaps or carrier layer sections 5, 6 extending therefrom and being separated by the slit 3. The flaps or sections 5, 6 of the carrier layer 1 separated by the slit 3 are designed to be affixed on either side of the puncture site of the needle and over the sidewardly extending attachment flanges thereof for the sake of facilitating needle securement.

The contact surface of the carrier layer 1 provided with the adhesive coating 2 is covered all over with three so-called release foil portions 7, 8, 9 made of silicone-treated paper, for example, and having free ends in the form of graspable, possibly outwardly bent flaps or pull tabs 10, 11, 12 serving both to simplify removal of the release foil from the tape and to secure the tape to the patient's skin without bacterial contamination occurring within the area around the puncture site of the hypodermic needle over which the tape is to be affixed. According to the invention, one 7 of the three release foil portions is applied across the adhesive coating 2 on the non-slit section 4 of the carrier layer, the other 8 over one 5 of the flaps formed by the slit 3 or the carrier layer section 5, and the third 9 over the other 6 of said carier layer sections. All gripping flaps 10, 11, 12 of the three release foil portions 7, 8, 9 are preferably located in close proximity to one another while suitably being outwardly folded from the plane of the tape for making them easily graspable at the moment of applying the tape to its site of use.

For enabling the release foil portions 7, 8, 9 to be completely detached from the carrier layer 1 but still remain fastened to the ends thereof, said foil portions are more firmly secured to the free end 4' of the non-slit section 4 of the carrier layer and to the free ends 5', 6' of the pull tabs or flap sections 5, 6 separated by the slit 3 than to the remainder of the carrier layer, which can be arranged with the aid of a perforation 13, 14, 15, an embossment or the like means. By the release foil being more strongly affixed to the free ends of the carrier layer, the hygienic conditions during needle securement will be improved by employing the inventive method of applying the needle securing tape, the inventive needle application in addition being significantly facilitated by the use of tapes having a thinner carrier layer. A perforation 13, 14, 15, an embossment or the like arrangement will in fact create an indication of bending, enabling thereby the release foil also to serve as application means for the tape until it is finally detached from the adhesive coating of the carrier layer.

In order to increase the friction of the gripping flaps 10, 11, 12 of the release foil, said flaps can be given an embossed surface on their side treated with release agent.

After manufacture, the inventive tape for securing a hypodermic needle is suitably packed in the form of individually wrapped items for the sake of simplifying and maintaining safe sterilization thereof up to the moment of application to the site of use.

The invention is not restricted to the exemplary embodiment described in the foregoing and illustrated in the drawing but can be modified in various manners within the scope of the patent claims.

We claim:

1. In a hypodermic needle attachment tape which comprises a carrier layer (1) for attachment to the skin of a patient across an inserted hypodermic needle, and which carrier layer is divided partially in one direction by a slit (3) and is provided with an adhesive coating (2) on the side thereof which contacts the hypodermic needle and the patient's skin, and which adhesive coating (2) is covered by sheets of release foil (7-9) the mutually adjacent ends of which sheets are free and are disposed adjacent each other and serve as pull tabs for the removal of said sheets, the adhesive coating (2) for application to the patient and to the hypodermic needle extending over only one side of the whole of the carrier layer (1), one of the release sheets (7) extending over the non-slitted section (4) of the carrier layer; the improvement in which each of two further separate release sheets (8,9) extends over a respective section (5,6) of the carrier layer separated by said slit (3) and is provided with a respective separate pull tab (10,11), said separate pull tabs (10,11) being disposed side by side of each other and being disposed endwise beyond their respective release sheets in a direction parallel to said slit (3).

2. A tape according to claim 1, in which the release sheets are more firmly secured to the free ends of the non-slit section of the carrier layer and to the sections of said layer separated by the slit than to the remainder of the carrier layer.

* * * * *